United States Patent [19]

Bentley et al.

[11] 4,107,433

[45] Aug. 15, 1978

[54] PHTHALIDYL ESTER OF 3-CARBOMOYLOXY CEPHALOSPORIN DERIVATIVES

[75] Inventors: Peter Hubert Bentley, Rudgwick; John Peter Clayton, Horsham, both of England

[73] Assignee: Beecham Group Limited, England

[21] Appl. No.: 755,159

[22] Filed: Dec. 29, 1976

Related U.S. Application Data

[62] Division of Ser. No. 549,374, Feb. 12, 1975, abandoned.

[30] Foreign Application Priority Data

Feb. 21, 1974 [GB] United Kingdom ............... 7860/74

[51] Int. Cl.² ................ C07D 501/30; C07D 501/34

[52] U.S. Cl. ...................................... 544/30; 544/22; 424/246

[58] Field of Search ............... 260/243 C; 544/30, 22

[56] References Cited

U.S. PATENT DOCUMENTS

| | | | |
|---|---|---|---|
| 3,951,954 | 4/1976 | Murakami et al. | 260/243 C |
| 3,963,704 | 6/1976 | Ferres | 260/243 C |

*Primary Examiner*—Donald G. Daus
*Assistant Examiner*—David E. Wheeler
*Attorney, Agent, or Firm*—Jacobs & Jacobs

[57] ABSTRACT

Phthalidyl and substituted phthalidyl esters of certain cephalosporins are absorbed by the oral route into the serum, where they are hydrolyzed to the parent antibacterially active cephalosporin.

3 Claims, No Drawings

PHTHALIDYL ESTER OF 3-CARBOMOYLOXY CEPHALOSPORIN DERIVATIVES

This is a division of Ser. No. 549,374 filed Feb. 12, 1975 now abandoned.

This invention relates to phthalidyl and certain substituted phthalidyl esters of cephalosporins, and to a method for their preparation. Such esters are valuable in that they are absorbed by the oral route into the serum, where they are hydrolysed to release the parent antibacterially active cephalosporin.

According to the present invention there is provided a cephalosporin ester of formula (I) and pharmaceutically acceptable acid addition salts thereof:

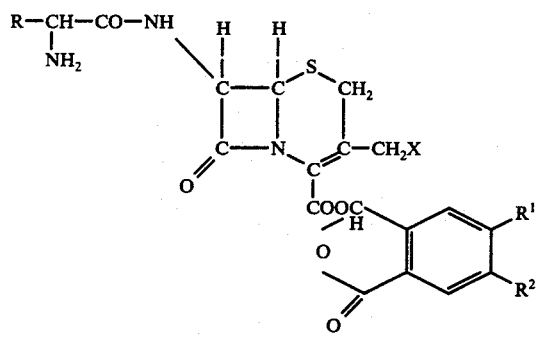

wherein R is a phenyl, 4-hydroxyphenyl, 3,4-dihydroxyphenyl, 3-chloro-4-hydroxyphenyl, 2- or 3-thienyl or dihydrophenyl group; X is an acetoxy, carbamoyloxy or heterocyclic thio group; and $R^1$ and $R^2$ are hydrogen or methoxy groups, provided that when $R^1$ and $R^2$ are both hydrogen and X is acetoxy, then R is not phenyl.

Suitable acid addition salts of the compounds of formula (I) include, for example, inorganic salts such as the sulphate, nitrate, phosphate, borate and hydrohalides, e.g. hydrochloride, hydrobromide and hydroiodide and organic salts such as the acetate, oxalate, tartrate, maleate, citrate, succinate, benzoate, ascorbate and methanesulphonate.

The group X may be inter alia a heterocyclic thio group. Examples of particular X groups include the following:

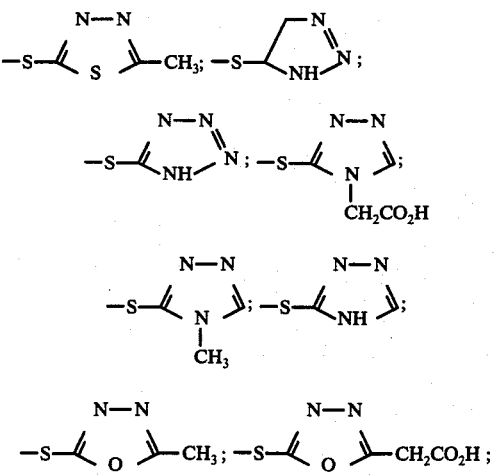

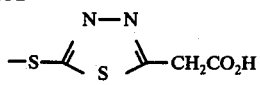

Preferably, the group X is (2-methyl-1,3,4-thiadiazol-5-yl) thio, (1-methyl-(1H)-1,2,3,4-tetrazol-5yl) thio, (2-methyl-1,3,4-oxadiazol-5-yl) thio, or (1H-1,3,4-triazol-5-yl) thio.

The compounds of formula (I) may be prepared by reacting a compound of formula (II):

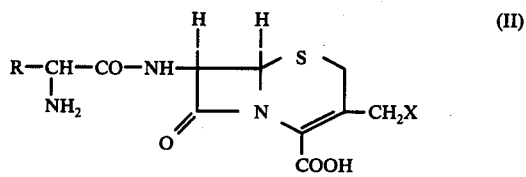

or a reactive esterifying derivative thereof, wherein R and X are as defined with respect to formula (I), with a compound of formula (III):

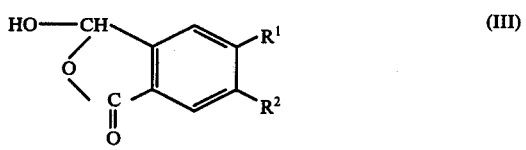

or a reactive esterifying derivative thereof, wherein $R^1$ and $R^2$ are as defined with respect to formula (I) and wherein any reactive groups such as amino and hydroxy may be blocked, and thereafter, if necessary:

(i) converting a $\Delta^2$ isomer into the desired $\Delta^3$ isomer;
(ii) removing any blocking group in the acyl side chain.

By "reactive esterifying derivative" in relation to compounds (II) and (III) above, we mean derivatives of (II) and (III) which when reacted together take part in a reaction with the consequent formation of an ester linkage of formula (I). Many methods of esterification are known from the literature. For example, the esterification reaction defined above may be achieved by reacting an N-protected cephalosporanic acid of formula (II) or a salt thereof with a 3-halophthalide or 3-halo-5,6-dimethoxyphthalide. Examples of suitable salts include alkali metal salts such as sodium or potassium, or a trialkylammonium salt such as triethylammonium.

With this route it is preferable to protect the α-amino group in the side chain of compound (I) prior to the esterification reaction. In such cases any of the amino protecting groups known from the literature on the synthesis of α-aminobenzyl penicillin or α-aminobenzyl cephalosporanic acids are suitable.

Examples of protected amino groups include the protonated amino group ($NH^+_3$) which after the acylation reaction can be converted to a free amino group by simple neutralisation; the t-butyloxycarbonyl, benzyloxycarbonylamino group or substituted benzyloxycarbonyl-amino groups which are subsequently converted to $NH_2$ by catalytic hydrogenation; and various groups which after the acylation reaction regenerate the amino group on mild acid hydrolysis. (Alkaline hydrolysis is not generally useful since hydrolysis of the ester group takes place under alkaline conditions.)

Example of a protected amino group which may subsequently be converted to NH$_2$ by mild acid hydrolysis include enamine groups of general formula (IV) or tautomeric modifications thereof, and α-hydroxyarylidene groups of general formula (V) or tautomeric modifications thereof:

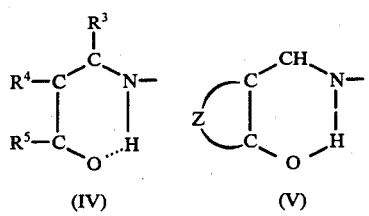

In structures (IV) and (V) the dotted lines represent hydrogen bonds. In structure (IV) R$^3$ is a lower alkyl group, R$^4$ is either a hydrogen atom or together with R$^3$ completes a carbocyclic ring, and R$^5$ is a lower alkyl, aryl, or lower alkoxy group. In structure (V) Z represents the residue of a substituted or unsubstituted benzene or naphthalene ring.

An example of a "protected amino" which can be converted to NH$_2$ after the esterification reaction is the azido group. In this case, the final conversion into NH$_2$ may be brought about by either catalytic hydrogenation or electrolytic reduction. Alternatively the amino group may be blocked as the nitro group which is later converted to the amino group by reduction.

In the above process, the esterification reaction may cause a double bond shift to position 2 of the cephem nucleus, thereby producing a mixture of 2-cephem and 3-cephem isomers. If this happens, the 2-cephem/3-cephem mixture can be converted to the 3-cephem isomer by oxidation of the mixture to the sulphoxide followed by reduction. This is, of course, a standard method for the preparation of 3-cephems from 2-cephems, and is described for example in British Pat. No. 1,280,693. One such method is treatment with triphenylphosphine and acetyl chloride.

The compounds of this invention may also be prepared by reacting a compound of formula (VI)

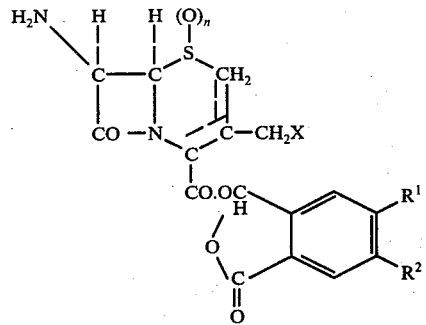

wherein the dotted line represents a bond in the 2- or 3-position and n is 0 or 1 with a reactive N-acylating derivative of an acid of formula (VII):

wherein R, R$^1$, R$^2$ and X are as defined in formula (I) and wherein any reactive groups, such as amino and hydroxy groups may be blocked, and thereafter, if necessary carrying out one or more of the following steps:
 (i) converting a Δ$^2$ isomer into the desired Δ$^3$ isomer;
 (ii) reduction of a sulphoxide compound to form the desired sulphide compound;
 (iii) removal of any blocking groups in the acyl side chain;

A reactive N-acylating derivative of the acid (VII) is employed in the above process. The choice of reactive derivative will of course be influenced by the chemical nature of the substituents in the acid.

Suitable N-acylating derivatives include an acid halide, preferably the acid chloride, or a mixed anhydride. For this purpose particularly convenient mixed anhydrides are the alkoxyformic anhydrides.

Alternative N-acylating derivatives of acid (VII), are activated esters. Such activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (VII) include the reactive intermediate formed by reaction in situ with a carbodiimide or carbonyldiimidazole, but the literature on the preparation of semi-synthetic penicillins contains examples of other reactive N-acylating derivatives of acids suitable for coupling to 6-APA, for example the acid azide.

Again any of the known N-protecting groups may be employed (especially the t-butoxycarbonyl group).

Compounds of formula (I) wherein X is a heterocyclic thio group may be prepared by displacing the acetoxy group from the corresponding 3-acetoxymethyl compound of formula (I) (i.e. X=acetoxy) by nucleophilic displacement thiol.

The compounds of this invention, wherein X is carbamoyloxy, may also be prepared from the corresponding 3-hydroxymethyl compound by carbamoylation of the hydroxy group. In such a process, a compound of formula (VIII):

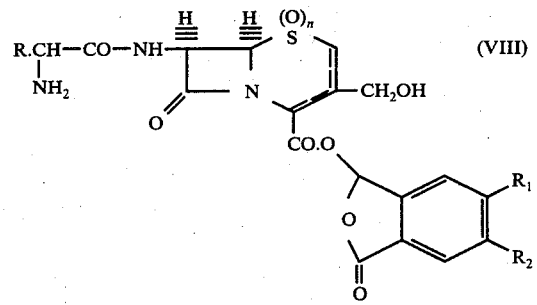

wherein the dotted line represents a bond in the 2- or 3-position, n is 0 or 1, R, R$^1$ and R$^2$ are as defined in formula (I), and wherein any reactive groups may be blocked, is reacted with an isocyanate of formula R$^6$NCO where R$^6$ is a group which is removable from the reaction product with compound (VIII) under mild conditions to give compound (I) and thereafter, if necessary, one or more of the following steps is carried out:
 (i) converting a Δ$^2$ isomer into the desired Δ$^3$ isomer;
 (ii) reduction of a sulphoxide compound to form the desired sulphide compound; and
 (iii) removal of any blocking groups in the acyl side chain;

Examples of compounds of formula $R^6NCO$ are disclosed in Belgian Pat. No. 794389. Suitable examples include trimethylsilyl isocyanate, $\beta,\beta,\beta$-trichloroethylisocyanate, and chlorosulphonyl isocyanate. The latter is preferred.

The intermediates of formula (VIII) may be prepared by the action of an esterase, for example citrus acetyl esterase, on the corresponding 3-acetoxymethyl cephem, [(I), $X=OCOCH_3$].

The following Examples illustrate the preparation of some of the compounds of this invention:

EXAMPLE 1

Phthalidyl 7-(2-thienylacetamido)-cephalosporanate (Epimers A and B) Method (a)

3-Bromophthalide (53.2g., 0.25 mole) was added to a stirred suspension of sodium 7-(2-thienylacetamido)-cephalosporanate (104.5g., 0.25 mole) in dry D.M.F. (850 mls) at 0°– 5°. After 65 mins. at 20° the almost clear solution was added to ice-water (12 liter) and the precipitated solid collected and washed with 2% $NaHCO_3$ solution, water, drying and evaporating, the crude product was reprecipitated from aqueous methanol and then refluxed in methanol for 15 mins. After cooling the insoluble epimer A (19.0g., 15%) m.p. 172°–5° was collected. A sample for analysis, m.p. 175.8° $[\alpha]_D^{25} = -40.8°$ (C=0.72, acetone) was crystallised twice from methanol: $\lambda_{max}^{KBr}$ 1780 (b), 1735, 1670, 1530, 1230, 975 $cm^{-1}$; $\lambda_{max}^{Dioxan}$ 272.5nm ($\epsilon$, 8150) and 280nm ($\epsilon$, 7,600) (shoulder). o ($CDCl_3$: 2.10) (s, 3H, $CH_3$) 3.51 and 3.56 (main peaks of ABq, 2H, —S-$CH_2$), 3.88 (s, 2H, —$CH_2$CO), 4.96 (d,J=4.7Hz, C6-H) and 5.03, 5.12 (main peaks of ABq, —$CH_2$-O) (3H in all), 5.85 (q,$J_{6,7}$-4.7Hz., $J_{7,NH}$-9Hz.,1H, C7-H), 6.52 (d,1H,$NH$), 7.0–8.1 (m, 8H, Ar-H and —O—C$H$-O—).

Found C, 54,62; H, 3.91; N, 5.13; $C_{24}H_{20}N_2S_2O_8$ (528) (requires C,54.54; H,3.81N, 5.30%.

The mother liquors from the reaction contained further quantities of the phthalidyl ester as a mixture of $\Delta^3$ and $\Delta^2$ isomers. Further quantities of the $\Delta^3$-isomer were isolated after oxidation-reduction as described below:

(i) Phthalidyl 7-(2-thienylacetamido)-cephalosporanate sulphoxide;

A mixture of phthalidyl 7-(2-thienylacetamido) cephalosporanate and its $\Delta^2$ isomer (14.4g) was dissolved in alcohol-free chloroform (230 mls) at 0°–5° and a solution of 3-chloroperbenzoic acid (5.09g) in chloroform (97 mls) was added over 15 mins. After 5 hours at 25°, the solution was washed with N-$NaHCO_3$, water, dried and evaporated.

The crude product was refluxed with methanol (100 mls) for 1 hour and the desired sulphoxide (10.3g, 70%) collected. $\lambda_{max}^{KBr}$ 1790 (b), 1740, 1680, 1515, 1230, 1050, 975 $cm^{-1}$. $\lambda_{max}^{Dioxan}$ 275nm ($\epsilon$,8220); o [$CD_3$)$_2$SO] 2.04 (s,3H, $CH_3$), 3.8 and 3.93 (main peaks of ABq, C2-H) and 3.87 (s, $CH_2$CO) (4H in all), 4.8 and 5.1 (main peaks of ABq, $CH_2$O) and 4.87, 4.96 (d,J=4, C6—H) (3H in all), 5.9 (m, 4 lines, $J_{7,NH}$ = 8, $J_{6,7}$ = 4, 1H, $C_7$—H), 7.0–8.0 (m,8H, Ar-H and O—C$H$—O) and 8.4 (d, J = 8, N$H$).

Found C,52.6; H, 3.7; N, 5.0; Calculated for $C_{24}H_{20}N_2O_9S_2$ (544): C, 52,9; H, 3.7; N, 5.1%.

(ii) Reduction of Sulphoxide

The sulphoxide (7.5g, 13.8 mole) was dissolved in D.M.F. (60 ml) and treated with triphenylphosphine (7.2g) and acetyl chloride (3.4 ml) at 0°–5°. After 1½ hours the pale yellow solution was treated with more triphenylphosphine (1.8g) and stirring continued for ½ hour more. Ice water (300 mls) and N-$NaHCO_3$ (100 mls) were then added and the mixture extracted with ethyl acetate (3 times).

These extracts were washed with water, dried and evaporated and the resulting brown residue triturated with ether repeatedly to remove excess triphenylphosphine. The insoluble residue was taken up into methanol, decolourised with activated charcoal and the filtrate allowed to crystallise. After refridgeration the insoluble solid (3.1g) was collected and addition of water to the liquors provided a second crop (4.4). Residual triphenyl-phosphine was freed from the combined material by trituration with ether to give the desired ester (4.2g, 58%) as a mixture of epimers A and B.

Method (b)

A solution of 7-(2-thienylacetamido) cephalosporanic acid (from 2.1g, 5m mole of the sodium salt), phthalaldehydic acid (0.75g) and dicyclohexylcarbodiimide (1.03g) in methylene dichloride (30 mls). After 4 hours at 0°–5° the insoluble solid was filtered and the filtrates washed with $NaHCO_3$ water, dried and evaporated. Chromatography of the residue provided epimer B (0.54g, 20%) m.p. 169°–171°. $[\alpha] D^{25} + 43.4$ (C,0.94, acetone), after crystallisation from methanol. o ($CDCl_3$): 2.06 (s, 3H, $CH_3$), 3.47 and 3.53 (main peaks of ABq, 2H, S-$CH_2$) 3.87 (s, 2H, $CH_2$CO), 4.7–5.3 (d and ABq, 3H, C6-H and $CH_2$O), 5.85 (dd, 1H, C7-H), 6.6 (d,N$H$), ), 7.0–8.0 (m, 8H, ArH and 0-C$H$-O).

Found. C, 54.4; H, 3.9; N, 5.3. Calculated for $C_{24}H_{20}N_2S_2O_8$: C, 54.5; H, 3.8; N, 5.3%.

EXAMPLE 2

(a) Phthalidyl 7-D-α-t-butyloxycarbonylaminophenylacetamido-3-(2'-methyl-1',3',4'-thiadiazol-5'-yl-thiomethyl) ceph-3-em-4-carboxylate 7-D-α-t-butyloxycarbonylphenylacetamido-3-(2'-methyl-1',3',4'-thiadiazol-5'-yl-thiomethyl) ceph-3-em-4-carboxylic acid, (3.00g) was dissolved in dry DMF (30 mls) at 0°–5° and treated with $Et_3N$ (0.96 ml) and then bromophthalide (1.62g) dissolved in DMF (10mls), was added. After 30 mins. at 0°–5° and 1 hour at 20°, the solution was poured into water (800 mls). The precipitated solid was washed well with water, dissolved in ethyl acetate and this solution washed with sodium bicarbonate, water, dried and evaporated. Precipitation from EtAc-petrol provided the desired ester as a buff coloured solid (2.3g, 47%).

This material was used without further purification. $\lambda_{max}^{CHCl_3}$ 3380, 1785 (b), 1700 (shoulder), 1690, 1485, 1160, 980$cm^{-1}$ $\lambda_{max}^{EtOH}$228nm )$\epsilon$, 18590) and 268 nm ($\epsilon$, 12620). $\delta$($CDCl_3$) 1.40 (s, 9H, Bu-H), 2.71 (s, 3H, thiadiazolyl-$CH_3$), 3.5–4.4 (m, 4H in all, S-$CH_2$), 4.9 (d), 5.2 (m), and 5.7 (m) (C$\alpha$, $C_6$ and $C_7$-H), 7.3–8.0 (m, Ar-H, O-C$H$-O and N$H$).

(b) Phthalidyl 7-D-α-aminophenylacetamido-3-(2'-methyl-1',3',4'-thiadiazol-5'-yl-thiomethyl) ceph-3-em-4-carboxylate The t-butoxycarbonyl derivative (1.50g) was treated at 5°–.0° with 98% aqueous trifluoroacetic acid (15 mls) for 1 hour when the solution was evaporated. Trituration of the residue with ether provided the essentially pure TFA salt (1.4g) $\lambda_{max}^{CHCl_3}$ 3400 – 2600, 1785 (b), 1700 (shoulder), 1675, 1620, 1540, 1190, 1140, 980 $cm^{-1}$ $_{max}$-$^{EtOH}$227nm ($\epsilon$, 16690) and 268nm ($\epsilon$, 12020).

Neutralisation of the TFA salt yielded the free amino ester.

EXAMPLE 3

(a) Phthalidyl 7-(D-α-t-butyloxycarbonylamino-p-hydroxy-phenylacetamido)-cephalosporanate The mixed anhydride was prepared from t-butyloxycarbonyl-D-p-hydroxyphenylglycine (2.53g, 9.50mmole), triethylamine (1.33 ml, 9.50mmole) and isobutylchloroformate (1.24 ml, 9.50mmole) at −10° to −15° in dry T,H,F. (30 mls) and $CH_2Cl_2$ (5 mls). After stirring for 10 mins. at this temperature a solution of ACA phthalide ester hydrochloride (4.18g, 9.50mmole) in $CH_2Cl_2$ 935 mls) containing triethylamine (1.33 ml) was added in one portion over 5 mins. maintaining the temperature at < −10°. The reaction was worked up in the usual way. The crude product (4.81g, 78%) which was precipitated from ethyl acetate-petrol ether, was purfied from some contaminating phthalide-7-isobutyloxycarbonyl-p-hydroxphenylacetamidocephalosporanate by chromatography on silica gel. The desired ester (2.5g) m.p. 126°–131° dec; had the following characteristics: $\lambda_{max}^{CHCl_3}$ 3380, 3300, 1780, 1740, 1685, 1495, 1365, 1220, 980cm$^{-1}$. $\lambda_{max}^{EtOH}$ 230nm (c, 20, 860) and 273nm (ε,9170). δ [(DC$_3$)$_2$SO] 1.38 (s, 9H,Bu-H), 2.0 (s, 3H, C$\underline{H}_2$, CO), 3.56, (bs, 2H,S-C$\underline{H}_2$); 4.6–5.3 (m,~4H, Cα-, C6- and OC$\underline{H}_2$), 5.7 (m, 1H, C7-H), 6.6, 6.75, 7.16 and 7.3 (dd, 4H, p-HO-C$_6$H$_4$), 7.5–8.1 (m, 5H, O-CH-O and phthalide-$\underline{H}$). 9.0 (m, ~2H, N$\underline{H}$) and 9.32 (s, 1H, O$\underline{H}$).

Found: C. 56.1; H, 4.8; N, 6.1. Calculated for $C_{31}H_{31}N_3O_{11}S$ (654): C, 56.9; H, 4.8; N, 6.4%.

Phthalidyl 7-(D-α-amino-p-hydroxyl-phenylacetamido)-cephalosporanate trifluoroacetate The protecting t-butyloxycarbonyl group was cleaved from the preceding derivative by treatment with 98% aqueous trifluoracetic acid over 1 hour. The desired trfluoroacetate, m.p. 144°–8° dec. was obtained in 92% yield as an amorphous solid: $\lambda_{Max}^{EtOH}$ 232nm (ε,20,625) and 273nm (ε,8740). δ [(CD$_3$)$_2$SO] 2.02 (s, 3H, C$\underline{H}_3$CO), 3.6 (bs, 2H, S-C$\underline{H}_2$), 4.7–5.2 (m,~4H, Cα-, C6- and O-C$\underline{H}_2$) 5.8 (m, 1H, C7-H), 6.75, 6.9, 7.3 and 7.4 (dd, 4H, p-HO-C$_6$H$_4$). 7.5–8.1 (m, —O—CH—O and phthalide —H and O$\underline{H}$) 8.7 (m, 3H, N$\underline{H}_3^+$) and 9.5 (m, N$\underline{H}$).

Found: C,47.8; H,3.6; N,5.7. Calculated for $C_{28}H_{24}N_3O_{11}SF_3 2H_2O$ C,47.8; H,4.0; N,6.0%.

EXAMPLE 4

By substituting 3-bromo-5,6-dimethoxyphthalide for 3-bromophthalide in the same procedure as in Examples 1, 2 and 3 the following compounds are obtained:

5$^1$,6$^1$-Dimethoxyphthalidyl-7-(2-thienylacetamido) cephalosporanate.

5$^1$,6$^1$-Dimethoxyphthalidyl-7-amino cephalosporanate hydrochloride.

5$^1$,6$^1$-Dimethoxyphthalidylcephaloglycinate

5$^1$,6$^1$-Dimethoxyphthalidyl 7(D-α-amino-p-hydroxyphenylacetamido)cephalosporanate.

5$^1$,6$^1$-Dimethoxyphthalidyl 7[D-α-aminophenylacetamido-3-(2-methyl-1$^1$,3$^1$,4$^1$-thiadizol-5-yl)thiomethyl]ceph-3-em-4-carboxylate.

EXAMPLE 5

(a) Phthalidyl 7-D-α-t-butyloxycarbonylaminophenylacetamido-3-(1$^1$-methyl-1$^1$-methyl-1$^1$-H-tetraxol-5$^1$-ylthiomethyl)ceph-3-em-4-carboxylate Sodium 7-D-α-t-butyloxycarbonylaminophenylacetamido-3-(1$^1$-methyl-1$^1$-H-tetrazol-5$^1$-ylthiomethyl)ceph-3-em-4-carboxylate (2.4g, 4.1mmole) was stirred in dry DMF (30 ml) and bromophthalide (0.85g, 4mmole) added with ice cooling. After 3 hours at 20° the mixture was poured into ice-water (300 ml) and the solid collected. An ethyl acetate solution of the latter was washed with dilute sodium bicarbonate, water, dried and evaporated. Precipitation of the residue from ethyl acetate — petrol provided the desired ester (2.0g, 74%), which was used without further purification. $\lambda_{Max}^{EtOH}$ 270nm (c, 7750); $_{max}^{CHCl_3}$ 3400, 1790, 1740, 1700(b), 1495, 1165, 980cm$^{-1}$.

Alternatively the crude product could be separated by silica gel chromatography into the 3-epimers.

(b) Phthalidyl 7-D-α-aminophenylacetamido-3-(1$^1$-methyl-1$^1$-H-tetrazol-5$^1$-yl-thiomethyl)ceph-3-em-4-carboxylate The preceding t-butyloxycarbonyl derivative (2.5g, 3.6mmole) was stirred for 0.75 hour at 10° with trifluoracetic acid (25 mls). After evaporation of the latter the residue was triturated with dry ether and the crude trifluoracetate of the title compound (2.48g, 97%) was collected and washed well with ether. The product showed one main zone on biochromatography, $R_f$ = 0.85 in n-butanol-ethanol-water. $\nu_{max}^{nujol}$ 1785, 1680, 1200cn$^{-1}$. δ(DMSO) 3.4.–4.1 (m, 2H, C2-H); 3.77 and 3.92 (2s, 3H, tetraxolyl-C$\underline{H}_3$), 4.1 – 4.6 (m, 2H, C$\underline{H}_2$S), 4.8 – 6.1 (m, 3H, C6, C7 and Cα-H), 7.2 – 8.2 (m, 10H, Ar-H + OC$\underline{H}$O). 8.9 (bs, 3H, N$\underline{H}_3^+$), 9.4 – 10.0 (m, N$\underline{H}$); $\lambda_{max}^{EtOH}$ 270nm (ε, 7410).

EXAMPLE 6

(a) Phthalidyl 7-D-α-t-butyloxycarbonylaminophenylacetamido-3-carbamoyloxy-methyl-3-cephem-4-carboxylate Sodium 7-D-α-t-butyloxycarbonylaminophenylacetamido-3-carbamoyloxy-methyl-3-cephem-4-carboxylate (2.1g, 4mmole) (see German OLS 2,550,151 is suspended in dry DMF (30 mls) and with ice cooling treated with bromophthalide (0.84g, 0.39mmole). After 1 hour at 20° ice-water (300 mls) is added and the solid collected. A solution of the latter in ethyl acetate is washed dilute sodium bicarbonate, water, dried and evaporated. Precipitation of the residue from ethyl acetate — petrol ether provides the desired ester (1.9g) which is used without further purification.

(b) Phthalidyl 7-D-α-aminophenylacetamido-3-carbamoyloxymethyl-3-cephem-4-carboxylate The foregoing crude ester (1.6g) is treated with chilled trifluoroacetic acid (15 mls) over 40 mins. Evaporation and trituration with ether gives the title compound as its trifluotactate (1.5g). This shows one major zone on biochromatography $R_f$ = 0.75 in n-Butanol-water.

We claim:

1. A cephalosporin ester of the formula:

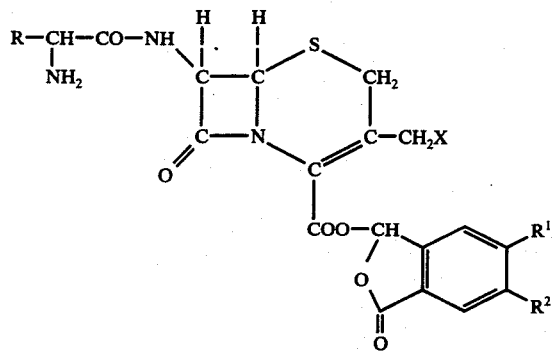

or a pharmaceutically acceptable acid addition salt thereof wherein R is phenyl, 4-hydroxyphenyl, 3-chloro-4-hydrophenyl,
2- or 3-thienyl or dihydrophenyl;
X is carbamoyloxy; and
$R^1$ and $R^2$ are hydrogen or methoxy.

2. The compound according to claim 1 which is phthalidyl 7-D-α-aminophenylacetamido-3-carbamoyloxymethyl-ceph-3-em-4-carboxylate.

3. A cephalosporin ester according to claim 1 in the form of an acid addition salt selected from the group consisting of the sulphate, nitrate, phosphate, borate, hydrochloride, hydrobromide, hydroiodide, acetate, oxalate, tartrate, maleate, citrate, succinate, benzoate, ascorbate and methanesulphonate.

* * * * *